United States Patent
Geebelen

(10) Patent No.: US 9,138,258 B2
(45) Date of Patent: Sep. 22, 2015

(54) ACETABULAR CUP REAMER GUIDE

(75) Inventor: Benjamin Geebelen, Haasrode (BE)

(73) Assignee: MATERIALISE N.V., Leuven (BE)

( * ) Notice: Subject to any disclaimer, the term of this patent is extended or adjusted under 35 U.S.C. 154(b) by 205 days.

(21) Appl. No.: 13/700,148

(22) PCT Filed: Jun. 1, 2011

(86) PCT No.: PCT/EP2011/059138
§ 371 (c)(1),
(2), (4) Date: Dec. 18, 2012

(87) PCT Pub. No.: WO2012/010366
PCT Pub. Date: Jan. 26, 2012

(65) Prior Publication Data
US 2013/0211407 A1    Aug. 15, 2013

Related U.S. Application Data

(60) Provisional application No. 61/350,127, filed on Jun. 1, 2010.

(30) Foreign Application Priority Data

Jun. 1, 2010    (GB) .................................. 1009116.3

(51) Int. Cl.
*A61B 17/56*    (2006.01)
*A61B 17/16*    (2006.01)
*A61B 17/17*    (2006.01)

(52) U.S. Cl.
CPC ................. *A61B 17/56* (2013.01); *A61B 17/16* (2013.01); *A61B 17/1631* (2013.01);
(Continued)

(58) Field of Classification Search
CPC ............... A61B 17/16; A61B 17/1631; A61B 17/1662; A61B 17/1664; A61B 17/1666; A61B 17/17; A61B 17/1739; A61B 17/1742; A61B 17/1746; A61B 17/56; A61B 2017/564; A61B 2017/568
USPC ................... 606/79–81, 86 R, 87, 91, 96–97; 623/22.12
See application file for complete search history.

(56) References Cited

U.S. PATENT DOCUMENTS 5,141,680 A    8/1992    Almquist et al.
5,192,539 A    3/1993    Van Der Marel et al.
(Continued)

FOREIGN PATENT DOCUMENTS

DE    10148022 A1 *    5/2003    ................ A61F 2/34
EP    2168507 A2    3/2010
(Continued)

OTHER PUBLICATIONS

The International Search Report, dated Nov. 17, 2011 for PCT Application No. PCT/EP2011/059138.
(Continued)

*Primary Examiner* — Larry E Waggle, Jr.
(74) *Attorney, Agent, or Firm* — EIP US LLP

(57) ABSTRACT

The present invention relates to guiding instruments for acetabular cup reamers, which allow for a much more accurate and precise reaming of the acetabular implant zone. The invention further provides combinations of acetabular cup reamers and guiding instruments therefor and methods for their manufacture and their use.

13 Claims, 7 Drawing Sheets

(52) U.S. Cl.
CPC ........ *A61B 17/1662* (2013.01); *A61B 17/1664* (2013.01); *A61B 17/1666* (2013.01); *A61B 17/17* (2013.01); *A61B 17/1739* (2013.01); *A61B 17/1742* (2013.01); *A61B 17/1746* (2013.01); *A61B 2017/564* (2013.01); *A61B 2017/568* (2013.01); *Y10T 29/49* (2015.01)

(56) References Cited

U.S. PATENT DOCUMENTS

| | | | |
|---|---|---|---|
| 8,808,302 B2* | 8/2014 | Roose et al. .................... | 606/96 |
| 2002/0099288 A1 | 7/2002 | Chang et al. | |
| 2005/0216020 A1 | 9/2005 | Orton | |
| 2010/0082035 A1* | 4/2010 | Keefer ............................ | 606/91 |
| 2012/0245647 A1* | 9/2012 | Kunz et al. ................. | 606/86 R |

FOREIGN PATENT DOCUMENTS

| | | | | |
|---|---|---|---|---|
| GB | 2390028 A | 12/2003 | | |
| WO | WO 2013152102 A1 * | 10/2013 | ............. | A61B 17/17 |

OTHER PUBLICATIONS

The Written Opinion of the International Searching Authority, dated Nov. 17, 2011 for PCT Application No. PCT/EP2011/059138.

The Written Opinion of the International Searching Authority, dated May 30, 2012 for PCT Application No. PCT/EP2011/059138.

The International Preliminary Report on Patentability, dated Sep. 6, 2012 for PCT Application No. PCT/EP2011/059138.

* cited by examiner

A

B

ACETABULAR CUP REAMER GUIDE

CROSS-REFERENCE TO RELATED APPLICATIONS

This application is a U.S. national phase of PCT Application No. PCT/EP2011/059138, filed Jun. 1, 2011, which claims priority to U.S. Application No. 61/350,127, filed Jun. 1, 2010 and British Application No. 1009116.3, filed Jun. 1, 2010.

FIELD OF THE INVENTION

The present invention relates to guiding instruments for acetabular cup reamers, combinations of acetabular cup reamers and guiding instruments therefor and methods for their manufacture and their use.

BACKGROUND

In hip replacement surgery, the acetabular cup implant area is prepared prior to positioning of the implant, in order to ensure a perfect fit thereof. Typically this involves removal of deteriorated or diseased bone surface, but also carving the opening to match the size of the implant to be fitted. This is performed using an acetabular cup reamer. This is typically a tool with a handle and a rotating head. Reamer heads of increasingly larger size (optionally provided as removable heads of one device) are used to enlarge the acetabulum during the reaming procedure.

Typically reaming starts at a diameter of about 6-8 mm less than the size of the implant, and sequential reaming is done with increments in 1-2 mm. However, the thickness of the acetabular wall should be taken into account. When thinning is present, the reamer should be pulled toward the opposite wall to avoid the generation of a rim defect. In order to ensure correct orientation of the opening, the position of the reamer should mimic the final position of the acetabular component. The finished acetabulum should have the cotyloid fossa removed and the acetabular rim snug against the finishing reamer.

An exact fit of the implant in the reamed acetabulum is critical as misalignment of the implant can lead to increased wear rate for the implant or improper seating of the implant leading to restricted leg movement and even hip dislocation.

Accurate reaming is however hampered by three important factors: a) the variability of patient-specific features, b) the limitation of the manipulation of the reamer by the surgical window, c) the limited visual access of the target area and d) the fact that precise manipulation of a rotary tool is difficult.

US 2002099288 describes a system which uses ultrasound imaging for guiding the placement and orientation of the implant relative to the anatomical landmarks surrounding the acetabulum such as the greater sciatic notch, the spine of the ischium, gemellus superior, obturator foramen, the anterior inferior spine and others.

US 2008009874 describes a reamer with a shaft onto which a one-piece guide is attached which includes a locator member which extends to a first portion of the bone providing a reference point relative to the reamer while the reamer engages a second portion of the bone during cutting. One reference point, however, does not suffice to restrict all degrees of freedom.

There is a need for reamers which can ensure precise and accurate reaming, to ensure optimal fitting of the acetabular cup implant.

SUMMARY OF THE INVENTION

The present invention provides guiding instruments for acetabular cup reamers, which allow accurate reaming of the acetabular cup zone.

Accordingly, a first aspect of the invention provides guiding instruments for an acetabular cup reamer which comprise one or more contact elements which fit onto areas of the bone surrounding the acetabular cup implant zone in at least three contact points and one or more connecting elements which allow reversible connection of the guiding instrument to a reamer. In particular embodiments, at least two of the one or more contact elements of the guiding instruments of the present invention form larger contact surfaces extending over specific areas of the bone surrounding the acetabular cup implant zone in at least three contact points. Typically, these contact elements comprise patient-specific surfaces.

In further particular embodiments, the one or more connecting elements allow a free rotation of the reamer around its longitudinal axis and limit the movement of the reamer along its longitudinal axis, such as to prevent the reamer from penetrating the bone to an excessively great depth. In certain particular embodiments, the guiding instrument is characterized by the presence of one or more locking elements which limit the movement of the reamer along its longitudinal axis, such as to prevent the reamer from penetrating the bone to an excessively great depth. In particular embodiments, at least one of the one or more locking elements are part of the guiding instrument. In certain embodiments, one or more of the locking elements are part of the one or more connecting elements. In particular embodiments, the one or more locking elements constitute a separate device, i.e. which is detachable from the guiding instrument.

The inventors more particularly provide combinations of guiding instruments and reamers which can be positioned securely onto the bone surrounding the acetabulum. This is ensured by ensuring that the contact elements fit specifically onto the bone.

In particular embodiments, the one or more contact elements of the guiding instruments according to the invention are designed such that the angle between the plane through the central axis of the circle formed by the acetabular rim and one contact point and the plane through the central axis of the circle formed by the acetabular rim and the adjacent contact point is never greater than 180° and, upon contacting said specific areas of the bone surrounding the acetabulum, ensure a tight fit of said guiding instrument on said bone. More particularly said contact elements contain a patient-specific surface which fits uniquely onto a specific area of the bone, such that there is only one correct position of the guiding instrument on the bone, i.e. the position wherein the contact elements are correctly positioned on their corresponding surface. In particular embodiments, guiding instruments are provided wherein the contact elements are designed such that, upon placement of the guiding instrument onto the bone, the guiding instrument (and optionally the acetabular cup reamer connected thereto) are forced into a position such that the reamer has the wanted orientation with respect to the pelvis. In further particular embodiments, a rotation of the guiding instrument around its central axis ensures that the guiding instrument can be placed in the correct position.

In particular embodiments, the guiding instruments according to the invention may comprise one or more fixation features allowing the attachment or connection of the guiding instrument to the bone by means of one or more fixation means, such as pins or screws.

In particular embodiments of the invention, the guiding instruments are characterized in that the connecting elements, which allow reversible connection of the guiding instrument to a reamer, form a separate device which optionally interlocks with the guiding instrument. More particularly, the connecting elements are detachable from the guiding instrument.

In particular embodiments, guiding instruments are provided as described herein which further contain a positioning feature allowing the passage of a positioning device placed in the bone surrounding the acetabulum. More particularly, the positioning device is a pin placed in the bone surrounding the acetabulum.

Most particularly, the guiding instruments according to the present invention are medical-image-based patient-specific instruments.

In particular embodiments, the guiding instruments according to the invention are modular devices comprising elements with a standard shape that can be adjusted to the shape of the bone.

The guiding instruments according to the present invention are provided for use in combination with an acetabular cup reamer. It is envisaged that the guiding instrument can be used with one or with a series of reamers.

A further aspect of the present invention provides combinations of an acetabular cup reamer and a guiding instrument according to the invention, wherein the acetabular cup reamer comprises a stem and a reaming element wherein the reaming element is fixed to the the stem and has a roughly hemispherical shape, and the guiding instrument comprises one or more contact elements which fit onto areas of the bone surrounding the acetabular cup implant zone in at least three contact points, wherein the one or more contact elements are designed such that the angle between the plane through the central axis of the circle formed by the acetabular rim and one contact point and the plane through the central axis and the adjacent contact point is never greater than 180° and, upon contacting the specific areas of the bone surrounding the acetabulum, ensure a tight fit of the guiding instrument on the bone.

In particular embodiments of the combinations of the present invention, two or more of the one or more contact elements of the guiding instruments of the present invention form larger contact surfaces extending over specific areas of the bone surrounding the acetabular cup implant zone in at least three contact points. More particularly, as detailed above these contact elements comprise a patient-specific surface which fits uniquely onto a specific area of the bone, such that there is only one correct position of the guiding instrument on the bone, i.e. the position wherein the contact elements are correctly positioned on their corresponding surface.

In particular embodiments of the combinations according to the invention, the contact elements present on the guiding instrument are designed such that, upon placement of the guiding instrument onto the bone, the guiding instrument (optionally with the acetabular cup reamer connected thereto) is forced upon placement into a position such that the guiding instrument has the wanted orientation with respect to the pelvis. In further particular embodiments, a rotation of the guiding instrument around its central axis ensures that the guiding instrument can be placed in the correct position.

The present inventors have further found that in order to allow correct placement of the guiding instrument and reamer combination of the present invention, more particularly in a limited surgical window, the stem of the reamer optimally comprises a hinge, which allows an independent movement of the end of the stem in a different orientation with respect to the reaming element of the reamer; more particularly the hinge may allow positioning of the end of the stem at an angle with respect to the rest of the stem and the reaming element e.g. during positioning of the guiding instrument/reamer combination of the invention in the surgical window. In this way, the presence of the hinge prevents the occurrence of a moment of force onto the guiding instrument, i.e. a tendency to twist or rotate the guiding instrument, when the surgeon handles the reamer in a non-optimal or sub-optimal position. This can be of interest upon introducing the device into a limited surgical window. In particular embodiments, this hinge is a universal joint, also called a universal coupling, a U joint, a Cardan joint, a Hardy-Spicer joint, or a Hooke's joint. In these embodiments, the universal joint allows the end of the stem to bend or rotate in any direction with regard to the rest of the stem and the reaming element, and thus allows to transmit an independent rotary motion of the end of the stem with regard to the rest of the stem and the reaming element.

In particular embodiments, the hinge allows rotation of the reaming element with respect to the end of the stem.

In further particular embodiments, the hinge allows a rotation of the reamer element with respect to the end of the stem of the reamer which is typically connected to a power tool, so as to ensure correct positioning of the reamer in the acetabular cup.

As detailed above, the combinations of the present invention are provided with one or more connecting elements. In further particular embodiments of the combinations according to the invention, one or more connecting elements are provided which reversibly connect the reamer to the guiding instrument and allow a free rotation of the reamer around its longitudinal axis.

In further particular embodiments, one or more locking elements are provided which limit the movement of the reamer along its longitudinal axis, such as to prevent the reamer from penetrating the bone to an excessively great depth. In certain particular embodiments, at least one of the one or more locking elements are part of the guiding instrument. In other particular embodiments, at least one of the one or more locking elements are part of the reamer. In certain particular embodiments, at least one of the one or more locking elements are part of the one or more connecting elements. In particular embodiments, the one or more locking elements constitute a separate device, i.e. which is detachable from the reamer and/or the guiding instrument.

In particular embodiments of the combinations according to the invention, at least one of the one or more connecting elements form part of the reamer. In particular embodiments, at least one of the one or more connecting elements are part of the guiding instrument.

In particular embodiments of the combinations of the invention, one or more connecting elements form a separate device, which is optionally detachable from the reamer and/or the guiding instrument. In yet further specific embodiments a combination of connecting elements is present on the reamer and guiding instrument and can optionally be detached there from. Accordingly, in particular embodiments, the one or more connecting elements constitute a separate device, i.e. which is detachable from the reamer and/or the guiding instrument. In particular embodiments, the connecting elements are a combination of elements which are reversibly present on the reamer and/or guiding instrument, wherein each element separately and/or the combination of elements can be detached from the reamer and/or the guiding instrument. Accordingly, in these embodiments, the connecting elements form a combination of elements that are removably present on the reamer and/or guiding instrument.

In particular embodiments of the combinations according to the invention, the guiding instruments comprise one or more fixation features allowing the attachment or connection of the guiding instrument to the bone by means of one or more fixation means, such as pins or screws.

In particular embodiments of the combinations according to the invention, the guiding instrument further contains a positioning feature allowing the passage of a positioning device placed in the bone surrounding the acetabulum. More particularly, the positioning device is a pin placed in the bone surrounding the acetabulum.

In particular embodiments of the combinations according to the invention, the guiding instrument is a medical-image-based patient-specific instrument.

In particular embodiments of the combinations according to the invention, the guiding instrument is a modular device comprising elements with a standard shape that can be adjusted to the shape of the bone.

Yet another aspect of the present invention provides methods for manufacturing the guiding instruments according to the invention.

In particular embodiments, methods for manufacturing a guiding instrument for an acetabular cup reamer are provided, which comprise (a) obtaining volume information of the pelvic bone and the acetabular implant to be placed therein, (b) identifying and selecting parts of the bone surrounding the implant zone which are suitable for use as a base for the contact elements of the guiding instrument, and (c) designing and producing a guiding instrument based on the information obtained in steps (a) and (b). More particularly the information obtained in step (b) is used in the design of suitable contact elements.

The devices for positioning and guiding acetabular cup reamers, and combinations thereof, according to the present invention allow for a much more accurate and precise reaming of an acetabular implant zone in comparison with the known surgical tools currently used in hip joint surgery. Moreover the devices of the invention can be more easily positioned and manipulated in a limited surgical window.

BRIEF DESCRIPTION OF THE DRAWINGS

The following description of the figures of specific embodiments of the invention is merely exemplary in nature and is not intended to limit the present teachings, their application or uses. Throughout the drawings, corresponding reference numerals indicate like or corresponding parts and features.

Figure 1:
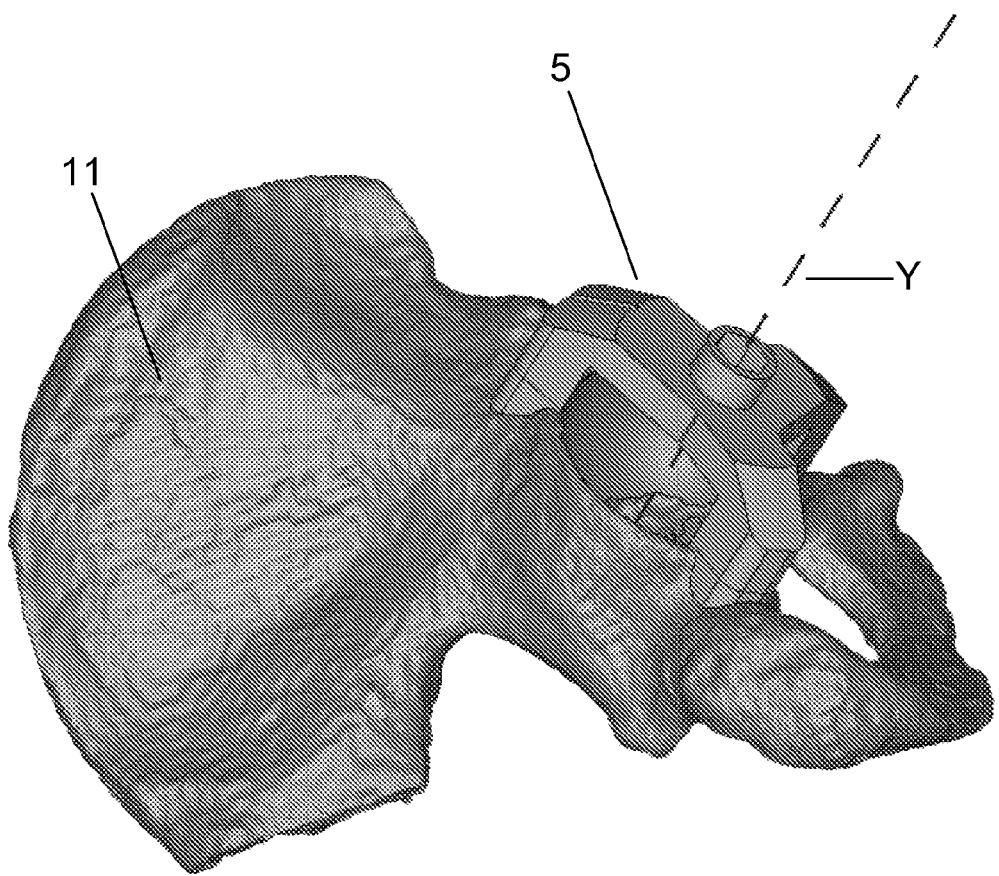
FIG. 1 provides a side top view of a guiding instrument (5) according to a particular embodiment of the invention, which is positioned on the pelvic bone (11). The central axis (Y) corresponds to the central axis of the implant, the central axis of the reamer when positioned in the guiding instrument and the central axis of the circle formed by the acetabular rim.

LIST OF REFERENCE NUMERALS USED IN THE FIGURES (1) Acetabular cup reamer
(2) Stem
(3) Reaming element
(4) Locking element
(5) Guiding instrument
(6) Contact element
(7) Connecting element
(8) Positioning feature
(9) Positioning device

(10) Hinge
(11) Pelvic bone
(Y) Central axis of the circle formed by the acetabular rim

DETAILED DESCRIPTION

The present invention will be described with respect to particular embodiments but the invention is not limited thereto but only by the claims. Any reference signs in the claims shall not be construed as limiting the scope thereof.

Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments of the invention described herein are capable of operation in other sequences than described or illustrated herein.

The terms or definitions used herein are provided solely to aid in the understanding of the invention.

The present invention relates to devices for implementing computer-aided surgical techniques and, more particularly, is directed to medical-image-based patient-specific surgical guides providing the ability to accurately ream a patient's acetabulum.

The majority of acetabular implants are currently placed using the press-fit technique, which consists of the following procedure:

The patient's acetabulum is reamed with a sequence of hemispherical reamers with increasing diameters, such that a hemispherical cavity is created where the implant should be placed. The last and largest reamer typically has a diameter smaller than that of the implant;
  The implant is attached to an impactor;
  Implant and impactor are placed upon the pelvis of the patient, such that the implant supports on the rim of the reamed cavity and the orientation of the implant is anatomically suitable;
  The impactor is hit with a hammer until the implant sits inside the reamed cavity;
  The implant is released from the impactor.

The acetabulum itself forms a good landmark for positioning the reamers. However, the surgeon has no means to control the depth to which is reamed except for visual verification. The surgical guides according to the present invention not only allow for optimal orientation of the reamer but also accurate control of the depth of reaming.

Accordingly, a first aspect of the invention provides guides for acetabular cup reamers. The guiding instruments according to the present invention can be securely fit in a specific position on the acetabulum. This is ensured by the presence of one or more contact elements.

In order to ensure stability of the guiding instrument, the one or more contact elements of the guiding instruments according to the present invention fit, engage or coincide, in at least three contact points thereon, with three or more areas on the patient-specific morphology of the pelvis bone surrounding the acetabular cup implant zone. In this way, the guiding instruments according to the present invention allow for an accurate and stable positioning of the acetabular cup reamer during reaming of the acetabulum.

In the context of the present invention reference is made to a "central axis", which corresponds to the central axis of the implant, in its optimal position. This central axis corresponds to the central axis of the acetabular cup, or the central axis of the circle formed (at least approximately) by the acetabular rim. In order to ensure a reamed acetabulum which allows placement of the implant in the desired position, the reamers should also carve out the bone. Typically a sequence of reamers is used, the last one of which is inserted into the bone by a downwards movement along the same axis. Accordingly, the central axis will correspond to the central axis of the guiding instrument, which corresponds to the orientation and the axis of movement of the reamer during reaming. The central axis is illustrated in FIG. 1 as "Y".

In particular embodiments, the contact elements of the guiding instruments according to the invention are designed in such a way that, upon positioning of the guiding instrument, rotational and/or translational movement of the guiding instrument in one or more directions is required so as to obtain the desired orientation onto the pelvis bone. In particular embodiments, this is ensured by the fact that the one or more contact elements fit, engage or coincide with surfaces having a patient-specific morphology on the bone surrounding the acetabulum. In further specific embodiments, the three-dimensional fit between the contact elements of the guiding instruments and the specific areas of the patient's pelvis bone surrounding the acetabular cup implant zone ensures the stability of the guiding instrument by preventing both translation and rotation (either uni- or bi-directionally) along and/or around a certain axis. Accordingly, in particular embodiments the contact elements of the guiding instruments according to the invention are designed in such a way that, upon positioning of the guiding instrument, the guiding instrument (and optionally the acetabular cup reamer connected thereto) is moved in one or more (i.e. different) directions, including for example rotation and/or translation in one or more (i.e. different) directions, until the reamer has the wanted orientation with respect to the pelvis.

In order to ensure stability of the guiding instrument, the contact points of the one or more contact elements are positioned such that the angle between the plane through the central axis of the circle formed by the acetabular rim and one contact point and the plane through the central axis and the adjacent contact point is less than or equal to 180°. In particular embodiments, this is ensured by the presence of at least three contact elements, whereby the angle between the plane through the central axis of the circle formed by the acetabular rim and one contact element and the plane through this central axis and the adjacent contact element is less than or equal to 180°. More particularly, it is envisaged that the guiding instruments comprise three contact elements which comprise contact points which are separated by an angle of about 120°. The contact elements typically span larger surfaces such that the distance between each the different contact elements is less than 120°.

In particular embodiments, the contact elements are provided such that one contact element comprises a surface which spans more than one of these contact points. Thus, in particular embodiments, at least two of the one or more contact elements of the guiding instruments which span the bone to at least three contact points form larger contact surfaces extending over specific areas of the bone surrounding the acetabular cup implant zone. In particular embodiments, the one or more contact elements of the guiding instruments of the invention extend over specific areas of the bone in at least one, such as at least two, or three or more different directions, to further ensure the stability of the position of the guiding instruments onto the pelvis bone. Indeed, in particular embodiments, the guiding instrument is designed based on information obtained from patient-specific medical images of the ischium, ilium and/or the pubis and uniquely matches with the specific bone geometry of the ischium, ilium and/or the pubis of the patient on which it is introduced indicating the patient-specific nature of the guiding instrument.

In particular embodiments, the guiding instruments of the present invention are modular instruments which comprise contact elements which can be adjusted to fit securely onto the patient-specific morphology of the pelvis bone surrounding the acetabular cup zone. For instance, in particular embodiments, the contact elements comprise individually adjustable elements which either prior to or during fixation are fitted onto the pelvic bone to ensure a tight fit onto the acetabulum. More particularly, the contact elements are elements which are movably connected to a central support structure and can be adjusted in height and/or can be moved, such as by rotation and/or translation, to ensure the most accurate fit with the particular parts of the pelvic bone.

In particular embodiments, one or more of the contact elements of the guiding instruments of the present invention are fixed and positioned to ensure a correct fit with a corresponding structure of the pelvic bone.

In particular embodiments, at least one of the contact elements of the guiding instruments of the present invention comprises, at the contact point, a patient-specific surface on the side facing the pelvis bone, which is exactly and fully complementary, i.e. fits specifically onto a specific anatomical area of the patient's pelvis bone surrounding the acetabular cup implant zone. This can be ensured by pre-operative planning based on images of the (reamed) acetabular cup zone. Accordingly, in particular embodiments, the guiding instrument is a medical-image-based patient-specific instrument. In further particular embodiments, this specific fit may involve a clearance between the surface of the contact elements and the bone, such as for example a clearance between the surface of the contact elements and the bone of between 0.1-1.0 mm. When the patient-specific surfaces of the contact elements are contacted with or positioned opposite to their corresponding complementary surfaces of the patient's pelvis bone, the surfaces fit, mate and/or engage, thereby fixing the guiding instrument, and thus also the reamer connected or attached thereto, into the correct and desired position.

Typically, a patient-specific surface of a contact element is selected based on anatomical features present on the pelvis bone surrounding the implant zone. In particular embodiments a patient-specific surface is selected based on anatomical features present on one or more of the ilium part, the pubis part and the ischium part of the pelvic bone. However, it is also envisioned in particular embodiments, that features are introduced onto the patient's bone to allow the generation of patient-specific surfaces on the contact elements based thereon.

In particular embodiments as detailed above, the one or more contact elements of guiding instruments according to the invention are designed such that, upon correct placement of the guiding instrument onto the bone, i.e. a placement in which there is a tight interlock between the contact elements of the guiding instrument and the corresponding anatomical areas of the patient's pelvic bone, the guiding instrument is forced into a position such that the reamer connected thereto has the desired orientation with respect to the pelvis. In these embodiments a (limited) movement, such as rotation and/or translation, of the guiding instrument upon placement ensures that the one or more contact elements assume their correct position, i.e. ensure a fit or interlock between the (patient-specific) areas of the one or more contact elements of the guiding instruments and the corresponding anatomical areas of the patient's pelvis bone surrounding the acetabular cup implant zone. In this way, the stability of the guiding instrument is ensured by preventing both translation and rotation.

Apart from the requirement that they ensure a secure fit onto the pelvic bone, the size and shape of the contact elements of the guiding instruments according to the present invention are not critical to the invention. Typically the size and shape of the contact elements of the guiding instruments according to the present invention are determined by the three-dimensional surface of the pelvis bone surrounding the acetabular cup implant zone, more particularly of the pelvis bone surrounding the acetabular cup implant zone of the patient for which it is designed. In particular embodiments, the contact elements correspond to flanges, i.e. longitudinal structures which extend from the support structure of the guiding instruments of the invention in different directions and allow for a stable fitting of the guiding instruments onto the pelvis bone. In further particular embodiments the flanges extend in the direction of the ilium, ischium and the pubis, respectively. According to these embodiments, guiding instruments with at least three, more particularly guiding instruments with three flanges, are envisaged.

In certain embodiments, the guiding instruments according to the invention may comprise one or more positioning features allowing the passage of or connection to a positioning device. Typically, such a positioning device is introduced in the bone surrounding the acetabulum in a planned position after positioning of the guiding instrument in its appropriate position on the pelvic bone. The guiding instrument is then removed from the bone, leaving the positioning device in place, and connected to the reamer. The positioning device then facilitates repositioning of the guiding instrument and reamer combination. Optionally, the positioning device is further used in the remainder of the procedure, e.g. for orientation of the reamer and/or positioning of the implant. In particular embodiments, the positioning feature is a hole, a cannula, a channel or a slot, provided onto one or more of the contact elements, which allows the passage of a positioning device such as a guiding pin. In particular embodiments, the feature comprises at least a cylindrical hole. Additionally or alternatively, the positioning feature comprises a clasp or other fixation element which allows connection to a positioning device, such as a guiding pin.

More particularly the nature of the one or more positioning features of the guiding instruments (i.e. actual height or distance relative to the surface of the bone) is determined to ensure an adequate guidance of the guiding instrument by the positioning device or vice-versa.

As detailed above, in particular embodiments the positioning feature in the guiding instrument is designed for use in the placement of the positioning device in the bone. In these embodiments, the one or more positioning features can include a safety stop to prevent a positioning device from advancing beyond a planned depth into the bone.

The location of a positioning feature on the one or more contact elements of the guiding instruments according to the present invention is determined based on anatomical features of the bone, the desired position of the guiding instrument on the pelvic bone and the structure of the guiding instrument. The positioning feature(s) is(are) located on the guiding instrument such that the guiding instrument, when the positioning device is locked into the one or more positioning features, is in the desired position.

In particular embodiments, the guiding instruments according to the invention may comprise one or more fixation features allowing the attachment or connection of the guiding instrument to the bone by use of one or more fixation means, such as pins or screws. According to these embodiments, one or more fixation means are used to fix the guiding instrument on to the pelvic bone surrounding the acetabulum after positioning of the guiding instrument in its appropriate position. Typically, the location of such fixation features is planned during manufacture of the guiding instrument based on anatomical features of the bone and surrounding tissue, and taking into account the operation window.

In particular embodiments, the fixation feature is a hole, a cannula, a channel or a slot, provided in one or more of the contact elements, which allows the passage of a fixation means such as a fixation pin or screw. In particular embodiments, the feature comprises at least a cylindrical hole.

The guiding instruments according to the present invention are for use in combination with an acetabular cup reamer and for appropriate functioning it is required that guiding instrument and reamer are adequately, more particularly, reversibly connected. The "connection" between the guiding instrument and a reamer is one that ensures that the position of the reamer is determined by the position of the guiding instrument but which allows free rotation of the reamer along its axis. According to the present invention, this is ensured by one ore more connecting elements, which can be provided on the guiding instrument and/or on the reamer itself. In particular embodiments, the connecting elements ensure passage of the stem of the reamer through an opening which is part of, or connected to, the guiding instrument. More particularly, the connecting elements are detachable from the reamer and/or the guiding instrument. In more particular embodiments, the connecting elements form a combination of elements which are reversibly present on the reamer and/or guiding instrument, wherein each element separately and/or the combination of elements can be detached from the reamer and/or the guiding instrument.

Typically as described above, more than one reamer head is used in the preparation of the implant zone. The reamer heads can be provided as separate reamers or can be provided as interchangeable reamer heads of one reamer instrument. Accordingly, the connecting elements of the guiding instruments according to the present invention are designed to connect the guiding instrument either to one or to a series of reamers. Before the reaming, the guiding instrument is attached to the reamer by means of the connecting element(s). The connecting elements ensure that there is a tight connection such that the reamer is maintained in position during reaming. The connecting element(s) present on the guiding instruments according to the present invention allow rotation of the reamer around its longitudinal axis. In particular embodiments of the invention, the connecting element(s) themselves do not follow the rotation of the stem of the reamer. In particular embodiments, the one or more connecting element present on the guiding instrument according to the invention interact with one or more connecting elements on the reamer which ensure that the reamer can rotate around its longitudinal axis when the reamer is placed within the guiding instrument.

The one or more connecting elements of the guiding instruments according to the present invention can take different shapes and sizes. Typically, the guiding instruments according to the present invention comprise at least an opening, which allows passage of the stem of a reamer. More particularly, the opening is a shaft which is designed to allow the passage of the stem of a reamer. In particular embodiments, the shaft is designed to mate precisely with the circumference of the stem of a reamer. In further particular embodiments, one or more connecting elements form a separate device which interlocks with the guiding instrument. The one or more connecting elements are optionally provided with locking features which allow a tight lock with either the guiding instrument or the stem of the reamer.

In particular embodiments, the guiding instruments, the connecting elements and/or the reamers of the present invention are further designed such that upon placement of the reamer therein, the movement of the reamer along its longitudinal axis, more particularly, the movement of the stem downwards, i.e. towards the pelvic bone, is limited. This prevents the reamer from penetrating the bone to an excessive depth. Indeed, if the reamed cavity is too deep, the implant can not be placed in the desired position.

The feature of preventing movement of the reamer along its longitudinal axis is ensured, in particular embodiments, by one or more locking elements. These locking elements can be present on (or reversibly attached to) the reamer and/or the guiding instrument and/or the connecting element(s).

In particular embodiments, at least one of the one or more locking elements is part of the reamer. For example, a locking element present on (or reversibly attached to) the stem of the reamer is positioned such that it can interact with the guiding instrument or a connecting element when the reamer is placed in the guiding instrument. In particular embodiments, at least one of the one or more locking elements forms an integral part of the stem of the reamer. More particularly, the locking element corresponds to an expansion of the diameter of the stem or a protrusion present on the stem. The protrusion present on the stem of the reamer cannot pass through the shaft of the guiding instrument but rather interacts with the rim of the shaft.

In particular embodiments, at least one of the one or more locking elements is present on (or removably attached to) the guiding instrument. In further particular embodiments, the one or more of the locking elements that are present on the guiding instrument are incorporated into a connecting element. In a more particular embodiment, a locking element consists of the rim of the shaft of the guiding instrument which provides passage (but also limits the passage) of the stem of the reamer.

In particular embodiments as detailed above, the one or more locking elements constitute a separate device, i.e. which is detachable from the reamer and/or the guiding instrument and/or connecting element(s). More particularly, the one or more locking elements form a combination of elements which are reversibly present on the reamer and/or guiding instrument, wherein each element separately and/or the combination of elements can be detached from the reamer and/or the guiding instrument.

The location of the locking element on the guiding instruments and/or corresponding reamers according to the present invention is determined by the depth to which the reamer should be able to move. This can be determined by preoperative planning based on images of the acetabular cup zone prior to preparation and the projected position of the acetabular cup implant.

As detailed above, the guiding instruments according to the present invention are designed for use in combination with one or more acetabular cup reamers. Acetabular cup reamers comprising a stem and a reamer cup are known to the skilled person and it can be envisaged that the guiding instruments according to the invention can be adapted to function with known acetabular cup reamers. In particular embodiments, the guiding instruments according to the invention are designed for use in combination with an acetabular cup reamer which is provided with one or more appropriate connecting element(s) and/or locking element(s) which, upon placement of the reamer in the guiding instruments according to the invention ensure a tight fit of the acetabular cup reamer in the guiding instrument, while allowing rotation of the reamer and guiding instrument along its longitudinal axis and central axis, respectively. More particularly, it is envisaged that the stem of the reamer fits through an opening in the one or more connecting elements of the guiding element.

Accordingly, a further aspect of the invention provides for combinations of an acetabular cup reamer and guiding instrument, which, when interconnected ensure a tight fit of the acetabular cup reamer in the guiding instrument, while allowing rotation of the reamer along its longitudinal axis.

The combinations of an acetabular cup reamer and guiding instrument according to the present invention are characterized in that they comprise an acetabular cup reamer comprising a stem and a reaming element wherein the reaming element is optionally reversibly fixed to the stem and typically has a roughly hemispherical shape; and a guiding instrument for the acetabular cup reamer comprising one or more contact elements which fit onto areas of the bone surrounding the acetabular cup implant zone in at least three contact points. In particular embodiments of the combinations of the present invention, two or more of the one or more contact elements of the guiding instruments of the present invention form larger contact surfaces extending over specific areas of the bone surrounding the acetabular cup implant zone in at least three contact points. Thus, in particular embodiments of the combinations of the invention, the one or more contact elements of the guiding instruments extend over specific areas of the bone in at least one, such as at least two, or three or more different directions, to further ensure the stability of the position of the guiding instruments onto the pelvis bone. Indeed, in particular embodiments, the guiding instrument is designed based on information obtained from patient-specific medical images of the ischium, ilium and/or the pubis and uniquely matches with the specific bone geometry of the ischium, ilium and/or the pubis of the patient on which it is introduced indicating the patient-specific nature of the guiding instrument.

As described above, the contact elements of the guiding instruments according to the present invention are designed such that the angle between the plane through the central axis (Y) of the circle formed by the acetabular rim and one contact point and the plane through the central axis (Y) and the adjacent contact point is never greater than 180° and, upon contacting said specific areas of the bone surrounding the acetabulum, ensure a tight fit of said guiding instrument on said bone.

In particular embodiments of the combinations according to the invention as detailed above, the contact elements present on the guiding instrument are designed such that, upon placement of the guiding instrument onto the bone, the guiding instrument (optionally with the acetabular cup reamer connected thereto) is forced upon placement into a position such that the guiding instrument has the wanted orientation with respect to the pelvis.

In particular embodiments of the combinations according to the invention, this can involve movement of the guiding instrument (and optionally the acetabular cup reamer connected thereto) in one or more (i.e. different) directions, including for example rotational and/or translational movement of the guiding instrument (and optionally the acetabular cup reamer connected thereto) in one or more (i.e. different) directions, until the reamer has the wanted orientation with respect to the pelvis.

The combinations of an acetabular cup reamer and guiding instrument according to the present invention are further characterized in that they comprise one or more connecting elements which reversibly connect the reamer to the guiding instrument, and which allow a free rotation of the reamer around its longitudinal axis. The one or more connecting elements are provided on the acetabular cup reamer and/or on the guiding instrument. In particular embodiments, the guiding instrument comprises a connecting element which comprises at least a passage way for the reamer, more particularly for the stem of the reamer. In addition the reamer itself, more particularly the stem of the reamer comprises, in particular embodiments, one or more connecting elements which interact therewith. In further particular embodiments, the one or more connecting elements form a separate device which interlocks with the guiding instrument. In particular embodiments the one or more connecting elements provided on the reamer stem ensure a tight fit with the guiding instrument while allowing rotation of the reaming element around the central axis of the stem. Typically the one or more connecting elements present on the reamer comprise particular features which tightly interlock with the connecting element of the guiding instrument. In particular embodiments, the connecting element is a shaft provided on the reamer stem, which fits securely into a shaft provided on the guiding instrument.

In particular embodiments, the combinations of an acetabular cup reamer and guiding instrument according to the present invention are further characterized in that they comprise one or more locking elements which limit the movement of the reamer along its longitudinal axis, such as to prevent the reamer from penetrating the bone to an excessively great depth. The locking elements according to the invention are provided on the guiding instrument and/or on the reamer and/or on the connecting element(s). The different embodiments envisaged for the locking elements hereinabove equally apply to the combinations described herein.

More particularly, the one or more locking elements of the guiding instruments of the present invention can consist of the rim of the shaft of the guiding instrument which provides passage of the stem of the reamer.

Also, as described above, in particular embodiments, one or more locking elements provided on (or reversibly attached to) the stem of the reamer interacts with (a feature on) the guiding instrument such that movement in at least one direction along the axis of the reamer is limited. In particular embodiments the locking elements prevent movement of the reamer along its longitudinal axis in both directions. For example, in particular embodiments at least one of the one or more locking elements interacts with the reamer when placed in the guiding instrument, such as by interacting with (a locking element present on) the stem of the reamer. In particular embodiments the locking element is a protrusion provided on the stem of the reamer, which cannot pass through the shaft of the guiding instrument and/or connecting elements. In still further particular embodiments, the one or more locking elements constitutes a separate device, i.e. which is detachable from the reamer and/or the guiding instrument. In particular embodiments, the one or more locking elements form a combination of elements which are reversibly present on the reamer and/or guiding instrument, wherein each element separately and/or the combination of elements can be detached from the reamer and/or the guiding instrument.

The one or more locking elements optionally provided in the combination according to the present invention are in particular embodiments provided as an integral part of the one or more connecting elements.

In particular embodiments of the combinations according to the invention, the guiding instruments comprise one or more fixation features allowing the attachment or connection of the guiding instrument to the bone by means of one or more fixation means, such as pins or screws. In particular embodiments, the fixation feature is a hole, a cannula, a channel or a slot, provided in one or more of the contact elements, which allows the passage of a fixation means such as a fixation pin or screw.

The reamers provided in the combinations according to the present invention typically comprise a stem and a reaming element. Typically, the reaming element has a roughly hemispherical shape and is provided on its outer surface with cutting or scraping features which allow grating of bone when a rotating movement of the reaming element is ensured. Reaming elements or reamer cups with different cutting features are known to the skilled person. The reaming elements are typically removable or detachable from the stem and optionally interchangeable such that different reaming elements can be sequentially adapted onto one reamer stem.

The reamers provided in the combinations according to the present invention may further comprise a hinge in the stem of the reamer. As detailed above, this hinge allows independent movement of the end of the stem (opposing the reamer cup) and the reamer cup. Most particularly, the hinge may allow the movement of the stem to a position which forms an angle with the remainder of the stem. In this way, the hinge prevents that a moment of force occurs onto the guiding instrument, i.e. a tendency to twist or rotate the guiding instrument, when the surgeon handles the reamer in a non-optimal or suboptimal position. This can be of interest upon introducing the device into a limited surgical window. In particular embodiments, this hinge is a universal joint, also called a universal coupling, a U joint, a Cardan joint, a Hardy-Spicer joint, or a Hooke's joint. In these embodiments, the universal joint allows the end of the stem to bend or rotate in any direction with regard to the rest of the stem and the reaming element, and thus allows to transmit an independent rotary motion of the end of the stem with regard to the rest of the stem and the reaming element. In further particular embodiments, the hinge allows a rotation of the reamer element with respect to the end of the stem of the reamer which is typically connected to a power tool, so as to ensure correct positioning of the reamer in the acetabular cup.

Yet a further aspect of the present invention provides methods for manufacturing the guiding instruments according to the present invention.

As detailed above, in particular embodiments, the guiding instruments contain contact elements which are designed such as to ensure a tight fit of the guiding instrument on the bone surrounding the acetabulum. In particular embodiments, this is ensured by designing the guiding instrument or at least the contact elements based on pre-operative images of the bone surrounding the acetabular implant zone and the implant to be introduced therein. Accordingly, methods for producing the (patient-specific) guiding instruments according to the invention typically comprise the step of (a) obtaining volume information of the pelvic bone and the acetabular implant to be placed therein, (b) identifying and selecting parts of the bone surrounding the implant zone which are suitable for use as a base for the contact elements of the guiding instrument, and (c) producing a guiding instrument based on the information obtained in steps (a) and (b). In particular embodiments, step (b) comprises identifying and selecting parts of the bone surrounding the implant zone which contain sufficient features such that the fit of the contact elements with the bone is patient-specific.

Typically, the step of identifying and selecting parts of the bone surrounding the implant zone suitable for use as a base for the contact elements comprises selecting a part of the ilium, ischium and pubic bone of the pelvis suitable for use as a base for a contact element.

In particular embodiments, the methods of the present invention further comprise the step (b') of identifying the depth to be reamed with a particular reamer and the corresponding freedom of movement of the reamer which should be allowed by the presence of the locking element present on the guiding instrument and/or the acetabular cup reamer. This can be ensured by pre-operative planning. Accordingly, in particular embodiments the methods of the present invention comprise the step of producing a guiding instrument further taking into account the information obtained in this additional step (b'). In particular embodiments, this implies that the guiding instrument further comprises particular features which ensure that successive reamers can be moved to increasing depths.

The method for manufacturing the guiding instruments according to the invention may further comprise the step (b") of identifying and selecting a suitable position for the placement of a positioning device and the corresponding positioning feature in the guiding instrument. Again, this can be ensured by pre-operative planning. Thus, in particular embodiments the methods of the present invention comprise the step of producing a guiding instrument further taking into account the information obtained in this additional step (b").

In particular embodiments, the method for manufacturing the guiding instruments according to the invention further comprise step (b''') of identifying and selecting a suitable position for the fixation features, i.e. positions where a fixation means can be introduced into the pelvic bone to secure the guiding instrument thereto. Thus, in particular embodiments the methods of the present invention comprise the step of producing a guiding instrument further taking into account the information obtained in this step (b''').

It will be understood that the order of any one of steps b, b', b", or b''', where applicable, is not critical in the methods according to the invention.

The step of obtaining volume information of the pelvic bone and the acetabular implant to be placed typically comprises obtaining digital patient-specific image information which can be done by any suitable means known in the art, such as for example a computer tomography (CT) scanner, a magnetic resonance imaging (MRI) scanner, an ultrasound scanner, or a combination of Roentgenograms. A summary of medical imaging has been described in "Fundamentals of Medical imaging", by P. Suetens, Cambridge University Press, 2002.

In a particular embodiment, Additive Manufacturing (AM) techniques are used for manufacturing the guiding instrument according to the invention. Additive Manufacturing (AM) can be defined as a group of techniques used to fabricate a tangible model of an object typically using three-dimensional (3-D) computer-aided-design (CAD) data of the object. Currently, a multitude of Additive-Manufacturing techniques is available, including stereolithography, selective laser sintering, fused deposition modeling, foil-based techniques, etc.

Selective laser sintering uses a high-power laser or another focused heat source to sinter or weld small particles of plastic, metal, or ceramic powders into a mass representing the 3-dimensional object to be formed.

Fused deposition modeling and related techniques make use of a temporary transition from a solid material to a liquid state, usually due to heating. The material is driven through an extrusion nozzle in a controlled way and deposited in the required place as described among others in U.S. Pat. No. 5,141,680.

Foil-based techniques fix coats to one another by means of gluing or photo polymerization or other techniques and cut the object from these coats or polymerize the object. Such a technique is described in U.S. Pat. No. 5,192,539.

Typically AM techniques start from a digital representation of the 3-D object to be formed. Generally, the digital representation is sliced into a series of cross-sectional layers which can be overlaid to form the object as a whole. The AM apparatus uses this data for building the object on a layer-by-layer basis. The cross-sectional data representing the layer data of the 3-D object may be generated using a computer system and computer aided design and manufacturing (CAD/CAM) software.

The guiding instruments according to the present invention may be manufactured in different materials. Typically, only materials that are biocompatible (e.g. USP class VI compatible) with the human body are taken into account. Preferably the surgical template is formed from a heat-tolerable material allowing it to tolerate high-temperature sterilization. In the case selective laser sintering is used as an AM technique, the surgical template may be fabricated from a polyamide such as PA 2200 as supplied by EOS, Munich, Germany or any other material known by those skilled in the art may also be used.

Yet a further aspect of the present invention relates to the use of the guiding instruments and/or combinations according to the present invention. More particularly, the invention provides methods for accurate reaming of an acetabular cup zone, which methods involve the steps of placing the acetabular cup reamer in the guiding instruments according to the present invention, positioning the guiding instrument on the pelvic bone and ensuring that the one or more contact elements are adequately positioned on the pelvic bone to ensure a unique fit of the guiding instrument.

In particular embodiments, where the guiding instrument according to the present invention is provided with a positioning feature, the methods according to the invention may comprise the steps of positioning the guiding instrument on the pelvic bone and ensuring that the one or more contact elements are adequately positioned on the pelvic bone to ensure a unique fit of the guiding instrument, securing the positioning device in the pelvic bone based on the positioning feature, removing the guiding instrument from the pelvic bone, placing the reamer in the guiding instrument and repositioning the guiding instrument+reamer on the pelvic bone with the help of the positioning device.

The different aspects of the invention are illustrated herein by the following non-limiting embodiments.

Embodiment 1

Figure 2:
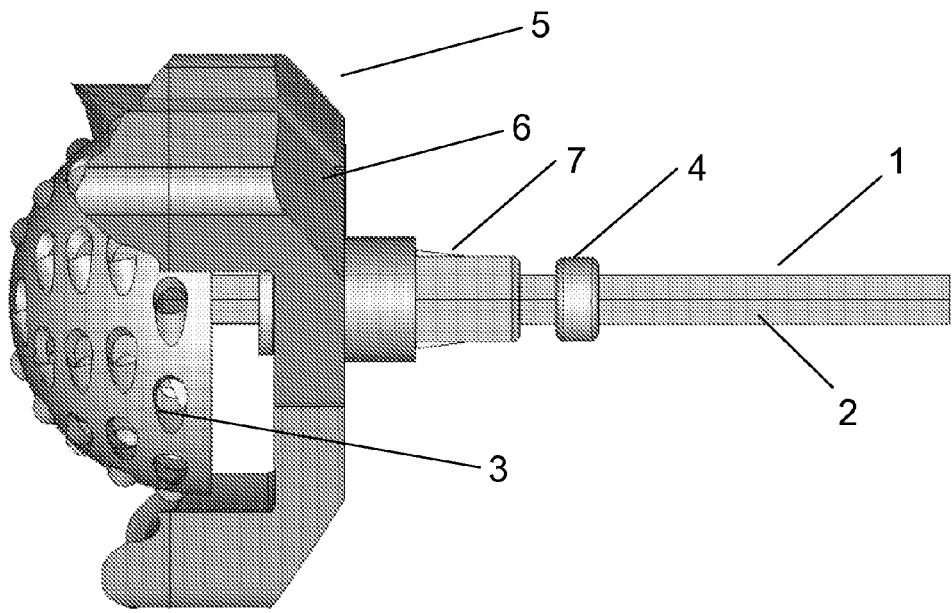
FIG. 2A illustrates a side view of the combination of an acetabular cup reamer (1) and a guiding instrument (5) wherein the reamer (1) comprises a stem (2), a reaming element (3), and a locking element (4); the guiding instrument comprises contact elements (6) and a connecting element (7) is provided which ensures connection of the stem (2) with the guiding instrument (5).
FIG. 2B illustrates a longitudinal section of part of the combination of an acetabular cup reamer (1) and a guiding instrument (5) according to a particular embodiment of the invention. The reamer (1) comprises a stem (2) and a reaming element (3). Only part of the guiding instrument (5) is shown to which a connecting element (7) is fixed. A locking element (4) is provided on the stem (2) of the reamer (1).
Figure 2:
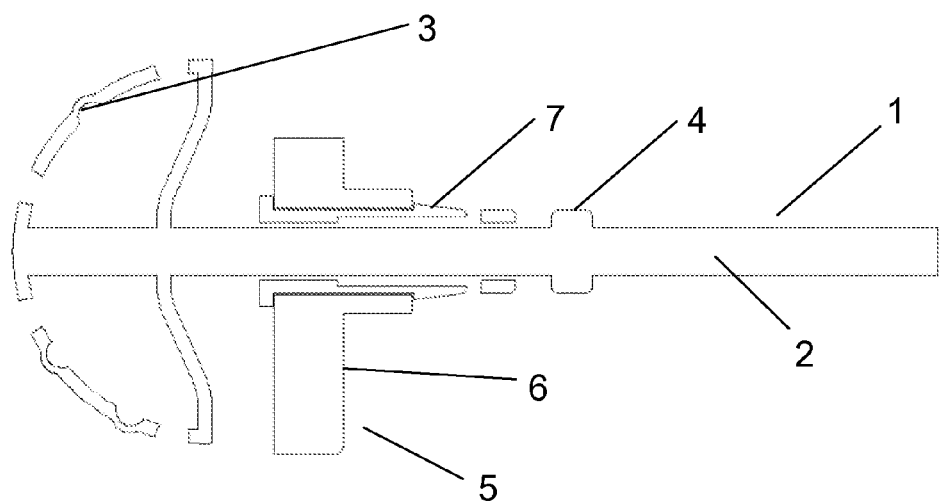

According to particular embodiments, a combination of an acetabular cup reamer and a guiding instrument is provided as illustrated in FIG. 2A. The combination comprises an acetabular cup reamer (1) and a guiding instrument (5). The acetabular cup reamer (1) comprises a stem (2) and a reaming element (3) wherein the reaming element is fixed rigidly to the end of the stem and has a roughly hemispherical shape. The guiding instrument (5) comprises one or more contact elements (6) which fit onto specific areas of the bone surrounding the acetabular cup implant zone. The combination further comprises a connecting element (7) reversibly fixed onto the guiding instrument (5) and which allows the passage of the stem (2) of the reamer (1), allowing the free rotation of the reamer around its longitudinal axis.

The stem of the reamer is provided with a locking element (4) which limits the movement of the reamer (1) along its longitudinal axis, such as to prevent the reamer from penetrating the bone to an excessively great depth.

Figure 3:
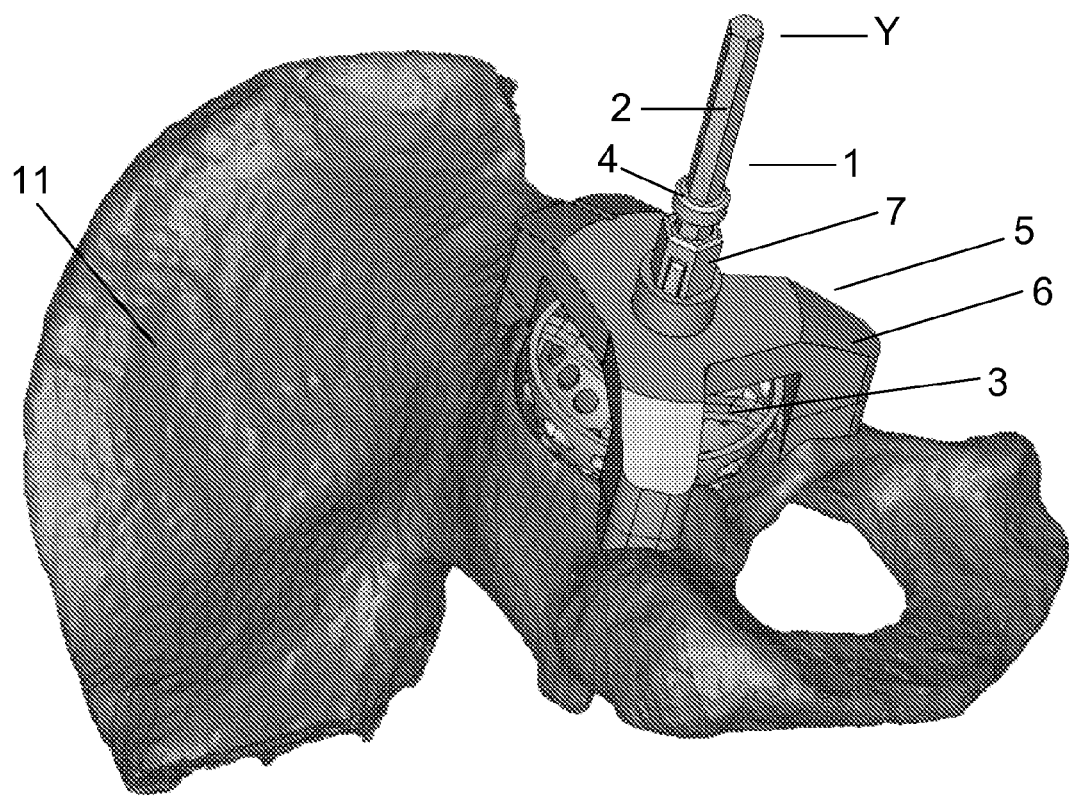
FIG. 3 provides a view from above of a combination of an acetabular cup reamer (1) and a guiding instrument (5) according to a further particular embodiment of the invention, positioned on the pelvic bone (11). The guiding instrument (5) comprises three contact elements (6). The guiding instrument (5) is shown with the connecting element (7) fixed thereto, which allows passage of the stem (2) of the reamer. The stem comprises a locking element (4).

FIG. 3 illustrates a side view of the combination of an acetabular cup reamer (1) and a guiding instrument (5) as described above, positioned on the pelvic bone (11). The guiding instrument (5) comprises three contact elements (6) which connect to the pelvic bone in at least three contact points. The three contact elements are designed such that the angle between the plane through the central axis (Y) of the circle formed by the acetabular rim, corresponding to the central axis of the reamer, and one contact point and the plane through the central axis (Y) and the adjacent contact point is not greater than 180°. The contact elements fit with specific areas of the bone surrounding the acetabulum, ensuring a tight fit of the guiding instrument on said bone; The guiding instrument (5) is shown with the connecting element (7) fixed thereto, which allows passage of the stem (2) of the reamer. The stem comprises a locking element (4).

FIG. 2B illustrates a longitudinal section of part of the combination of an acetabular cup reamer (1) and a guiding instrument (5) as described above. The reamer (1) comprises a stem (2) and a reaming element (3) fixed thereto. Part of the guiding instrument (5) is shown to which a connecting element (7) is fixed. A locking element (4) is provided on the stem (2) of the reamer (1).

Embodiment 2

Figure 4:
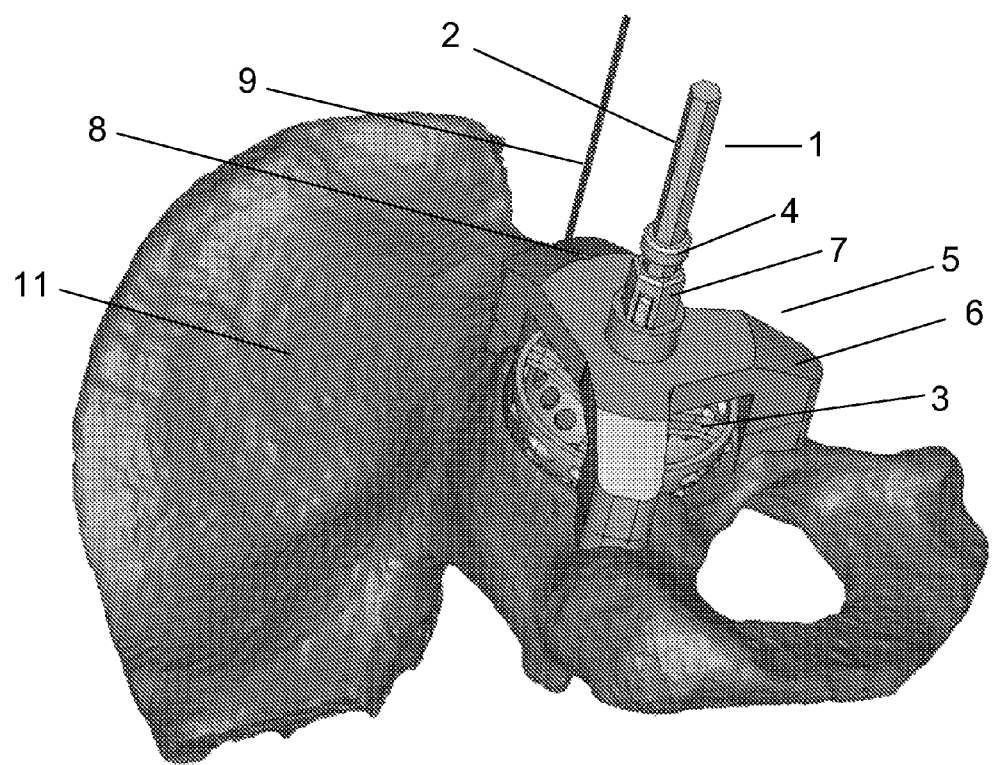
FIG. 4 provides a view from above of a combination of an acetabular cup reamer (1) and a guiding instrument (5) according to a further particular embodiment of the invention, positioned on the pelvic bone (11). The guiding instrument (5) comprises three contact elements (6). One of the contact elements (6) comprises a positioning feature (8), corresponding to a slit. A positioning device (9) is positioned through the positioning feature (8) into the pelvic bone (11). The guiding instrument (5) is shown with the connecting element (7) fixed thereto, which allows passage of the stem (2) of the reamer. The stem comprises a locking element (4).

FIG. 4 illustrates a combination of an acetabular cup reamer (1) and a guiding instrument (5) according to a further embodiment of the invention positioned on the pelvic bone (11). The guiding instrument (5) comprises three contact elements (6) which fit onto the pelvic bone in at least three contact points. One of the contact elements (6) comprises a positioning feature (8), corresponding to a slit. The positioning feature is used for the placement of a positioning device (9) into the pelvic bone. The contact elements (6) of the guiding instrument (5) fit with specific areas of the bone surrounding the acetabulum, ensuring a tight fit of the guiding instrument on said bone. The guiding instrument (5) is shown with the connecting element (7) fixed thereto, which allows passage of the stem (2) of the reamer. The stem comprises a locking element (4).

Figure 5:
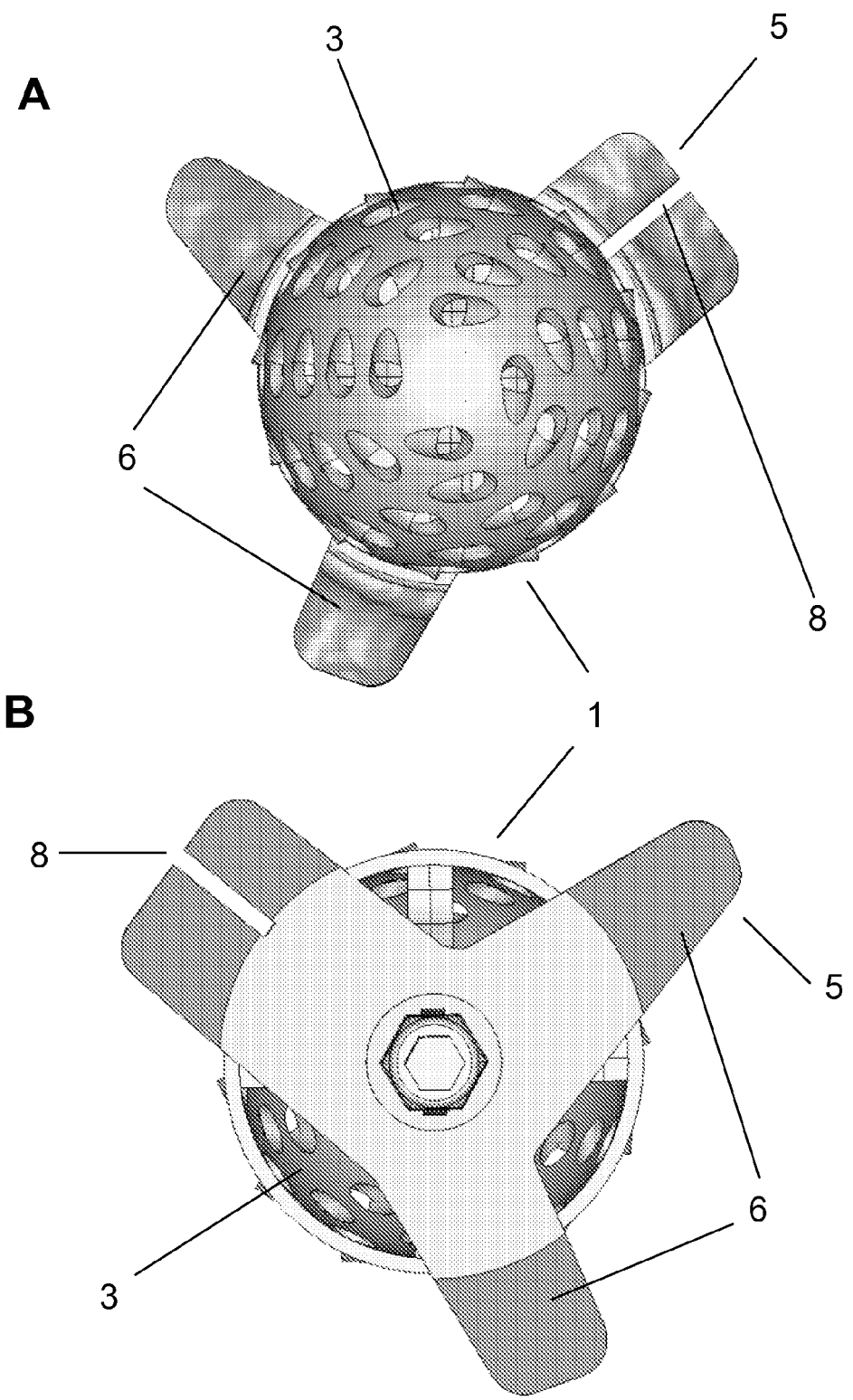
FIG. 5 provides a bottom (A) and top (B) view of a combination of an acetabular cup reamer (1) and a guiding instrument (5) according to an embodiment of the invention. In the bottom view (A), the reaming element (3) of the reamer (1) is primarily visible, as well as the patient-specific surfaces of the contact elements (6) of the guiding instrument (5). In the top view (B), the guiding instrument (5) is visible with its three contact elements (6). One contact element (6) contains a positioning feature (8).

FIG. 5 illustrates a top and bottom view of a combination of an acetabular cup reamer (1) and a guiding instrument (5) according to this embodiment. In the bottom view (A), the reaming element (3) of the reamer (1) is visible, as well as the patient-specific surfaces of the contact elements (6) of the guiding instrument (5). In the top view (B), the guiding instrument (5) is visible with its three contact elements (6).

Embodiment 3

Figure 6:
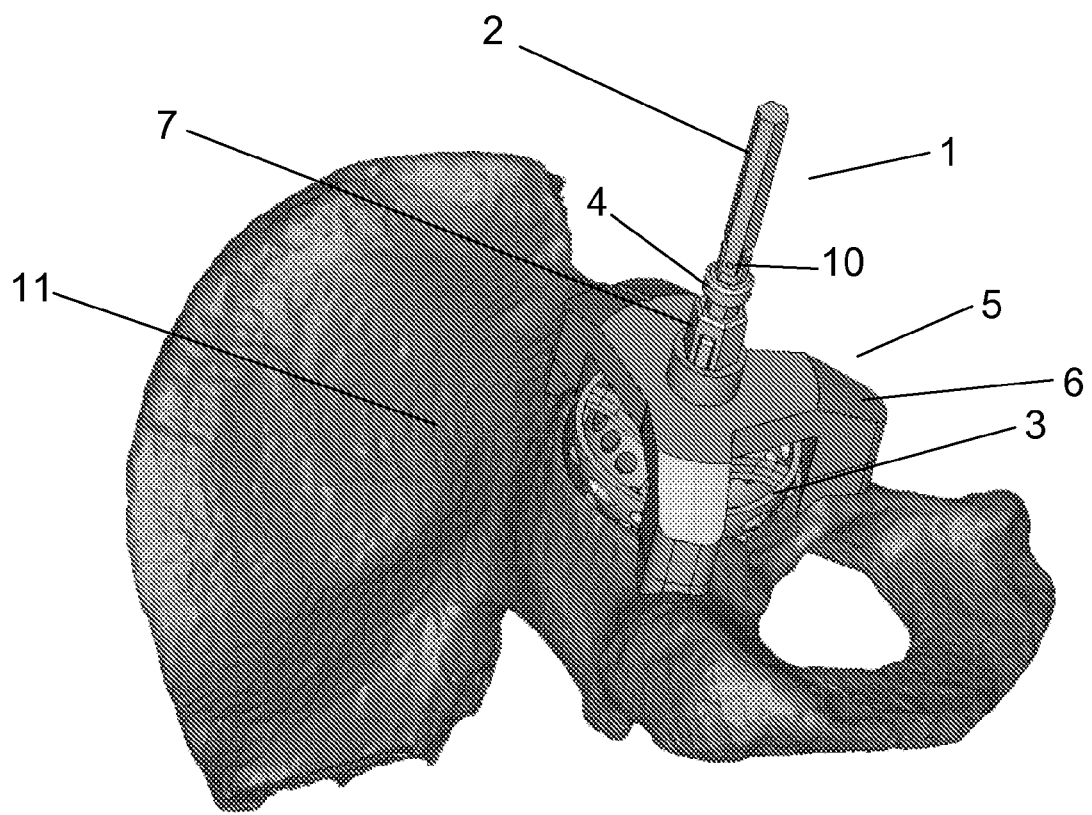
FIG. 6 provides a view from above of a combination of an acetabular cup reamer (1) and a guiding instrument (5) according to a further particular embodiment of the invention, positioned on the pelvic bone (11). The reamer (1) comprises a stem (2) and a reaming element (3). The stem comprises a hinge (10) and a locking element (4). The guiding instrument (5) is shown comprising three contact elements (6). A connecting element (7) is fixed to the guiding instrument.
Figure 7:
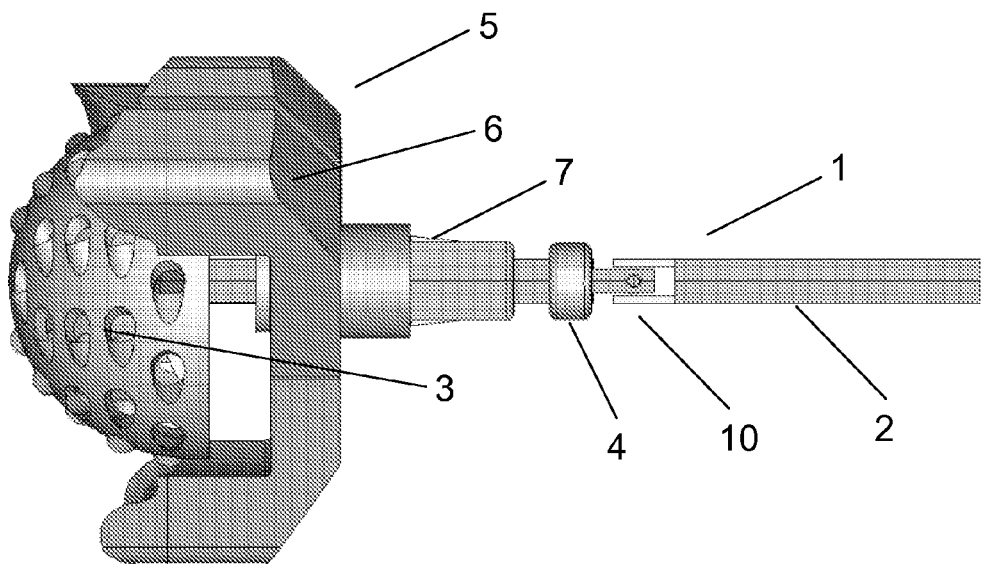
FIG. 7A illustrates a side view of the combination of an acetabular cup reamer (1) and a guiding instrument (5) wherein the reamer (1) comprises a stem (2), a reaming element (3); the stem comprises a hinge (10) and a locking element (4); the guiding instrument comprises contact elements (6) and a connecting element (7) is provided which ensures connection of the stem (2) with the guiding instrument (5).
FIG. 7B illustrates a longitudinal section of part of the combination of an acetabular cup reamer (1) and a guiding instrument (5) according to a particular embodiment of the invention. The reamer (1) comprises a stem (2) and a reaming element (3). The stem comprises a hinge (10) and a locking element (4). Only part of the guiding instrument (5) is shown to which a connecting element (7) is fixed.
Figure 7:
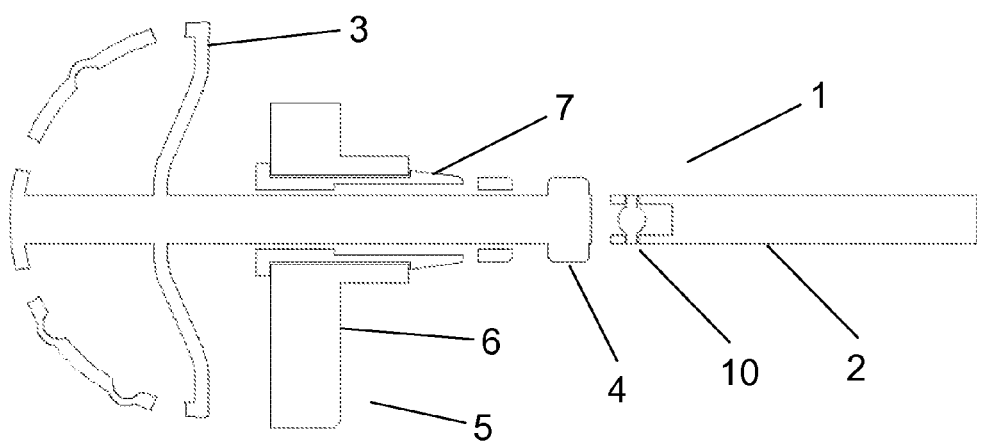

FIG. 6 illustrates a combination of an acetabular cup reamer (1) and a guiding instrument (5) according to a further particular embodiment of the invention, positioned on the pelvic bone (11). The reamer (1) comprises a stem (2) and a reaming element (3). The stem comprises a hinge (10) which allows the rotation of the reaming element with respect to the end of the stem which is inserted into a power tool. In this embodiment the hinge takes the form of a universal joint, which is further clearly illustrated in FIG. 7A.

The stem of the reamer further comprises a locking element (4). The guiding instrument (5) is shown comprising three contact elements (6). A connecting element (7) is fixed to the guiding instrument.

The invention claimed is:

1. A combination of an acetabular cup reamer (1) and a guiding instrument (5), which comprises:
   an acetabular cup reamer (1) comprising a stem (2) and a reaming element (3) wherein the reaming element (3) is fixed rigidly to the end of the stem (2) and has a roughly hemispherical shape and wherein the stem (2) comprises a hinge (10) comprising a universal joint, which allows movement of an end of the stem in a different orientation with respect to the reaming element (3) during operation of the reamer; and
   a guiding instrument (5) comprising one or more contact elements (6), wherein two or more of said contact elements (6) form larger contact surfaces extending over specific areas of a bone surrounding an acetabular cup implant zone in at least three contact points, wherein the one or more contact elements (6) are designed such that an angle between a plane through the central axis (Y) of the circle formed by an acetabular rim and one contact point and a plane through the central axis (Y) and an adjacent contact point is never greater than 180° and, upon contacting said areas of the bone surrounding the acetabular cup implant zone, ensure a tight fit of said guiding instrument (5) on said bone; and
   one or more connecting elements (7) which reversibly connect the reamer (1) to the guiding instrument (5), which allow a free rotation of the reamer (1) around its longitudinal axis.

2. The combination according to claim 1, wherein at least one of the one or more connecting elements is part of at least one of the reamer and the guiding instrument.

3. The combination according to claim 1, wherein said one or more connecting elements constitute a combination of elements or a separate device, which is detachable from at least one of the reamer and the guiding instrument.

4. The combination according claim 1, wherein said contact elements are designed such that, upon placement of the guiding instrument onto the bone, said guiding instrument and said acetabular cup reamer are forced into a position such that the reamer has a wanted orientation with respect to a pelvis.

5. The combination according to claim 4, wherein said guiding instrument, upon placement on the bone, can be rotated to obtain the position.

6. The combination according to claim 1, wherein said guiding instrument further contains a positioning feature allowing passage of a positioning device placed in the bone surrounding the acetabular cup implant zone.

7. The combination according to claim 6, wherein said positioning device is a single pin placed in the bone surrounding the acetabular cup implant zone configured to lock the guiding instrument in position without requiring additional pins.

8. The combination according to claim 1, wherein the guiding instrument is a medical-image-based patient-specific instrument.

9. The combination according to claim 1, wherein the guiding instrument is a modular device comprising elements with a standard shape that can be adjusted to a shape of the bone.

10. The combination according to claim 1, comprising one or more locking elements which limit movement of the reamer along its longitudinal axis, such as to prevent the reamer from penetrating the bone to an excessively great depth.

11. The combination according to claim 10, wherein at least one of the one or more locking elements is part of at least one of the reamer, the guiding instrument and the connecting elements.

12. The combination according to claim 10, wherein said one or more locking elements constitute a separate device, which is detachable from at least one of the reamer and the guiding instrument.

13. A method for the manufacture of the combination according to claim 1, which method comprises:
   (a) obtaining volume information of a pelvic bone and an acetabular implant to be placed therein,
   (b) identifying and selecting parts of the bone surrounding the acetabular cup implant zone which are suitable for use as a base for the contact elements of the guiding instrument, and
   (c) designing and producing the guiding instrument based on the information obtained in steps (a) and (b).

* * * * *